United States Patent [19]
Clemmer et al.

[11] Patent Number: 5,905,258
[45] Date of Patent: May 18, 1999

[54] HYBRID ION MOBILITY AND MASS SPECTROMETER

[75] Inventors: David E. Clemmer; James P. Reilly, both of Bloomington, Ind.

[73] Assignee: Advanced Research & Techology Institute, Bloomington, Ind.

[21] Appl. No.: 08/867,245

[22] Filed: Jun. 2, 1997

[51] Int. Cl.⁶ .................................................. H01J 49/40
[52] U.S. Cl. .......................................... 250/287; 250/282
[58] Field of Search ..................................... 250/287, 282

[56] References Cited

U.S. PATENT DOCUMENTS

| | | | |
|---|---|---|---|
| 3,812,355 | 5/1974 | Wernlund et al. | 250/283 |
| 3,845,301 | 10/1974 | Wernlund et al. | 250/287 |
| 3,902,064 | 8/1975 | Young | 250/287 |
| 4,261,698 | 4/1981 | Carr et al. | 250/287 |
| 5,070,240 | 12/1991 | Lee et al. | 250/288 |
| 5,117,107 | 5/1992 | Guilhaus et al. | 250/287 |
| 5,210,412 | 5/1993 | Levis et al. | 250/288 |
| 5,504,326 | 4/1996 | Reilly et al. | 250/282 |
| 5,510,613 | 4/1996 | Reilly et al. | 250/287 |
| 5,569,917 | 10/1996 | Buttrill, Jr. et al. | 250/287 |
| 5,622,824 | 4/1997 | Koster | 435/6 |

OTHER PUBLICATIONS

"Ion Mobility Spectrometry", Analytical Chemistry, vol. 62, No. 23, Dec. 1, 1990, pp. 1201 A–1209 A.
Abstract Proceedings of the 44th ASMS Conference, (1996), R. Guevremont, K.W.M. Siu and L. Ding, p. 1090.

*Primary Examiner*—Jack I. Berman
*Attorney, Agent, or Firm*—Beck, Michael & Beck, P.C.

[57] ABSTRACT

A hybrid ion mobility and time-of-flight mass spectrometer includes an ion source region coupled to an ion mobility spectrometer (IMS) which feeds directly into an ion accelerating region of a time-of-flight mass spectrometer (TOFMS). In one embodiment, the TOFMS is positioned relative to the IMS so that the flight tube axis of the TOFMS is perpendicular to the drift tube axis of the IMS. In an alternate embodiment, the TOFMS is positioned relative to the IMS so that the flight tube axis of the TOFMS is non-perpendicular to the drift tube axis of the IMS. In the alternate embodiment, a known quadrupole ion trap is positioned between the IMS and the TOFMS to provide the capability of controlling the injection of ion packets into the TOFMS. The ion source may be a MALDI source, an electrospray ionization source, or an ion trap positioned between the IMS and any known ion source. In each case, the IMS, TOFMS and ion sources are preferably controlled by a computer.

46 Claims, 9 Drawing Sheets

HYBRID ION MOBILITY AND MASS SPECTROMETER

FIELD OF THE INVENTION

The present invention relates generally to instrumentation for characterization of molecules based on their structures and mess-to-charge ratios as gas-phase ions, and more specifically to such instrumentation which provides for rapid and sensitive analysis of composition, sequence, and/or structural information relating to organic molecule, including biomolecules, and inorganic molecules The present invention is generally applicable to analysis of mixtures, such as extractions of natural products, mixtures of organic molecules found in petroleum products, particle sizing and analysis of mixtures associated with air quality control.

BACKGROUND OF THE INVENTION

Biological molecules, such as DNA, RNA, proteins, carbohydrates and glycoconjugates, are comprised of repeating subunits typically referred to as residues. The sequence of such residues ultimately defines the structure and function of the biomolecule and determines how it will interact with other molecules.

A central part of almost all conventional sequencing strategies is the analysis of complex sets of sequence-related molecular fragments by chromatography or by polyacrylamide gel electrophoresis (PAGE). PAGE-based automated sequencing instruments currently exist and typically require a number of fluorescent dyes to be incorporated into the base-specifically terminated biomolecule product, which is then processed through the polyacrylamide gel. The discrete-length product molecules are defected near the bottom of the gel by their emitted fluorescence following excitation by a radiation source.

Such automated instruments are typically capable of generating sequence information for biomolecules having 500 or more residues at a rate of 10–20 times faster than manual methods. However, both the manual and automated PAGE techniques suffer from several drawbacks. For example, both approaches are labor-intensive since a gel must be prepared for each sequencing run. Also, while automated PAGE systems may offer faster analysis times than a manual approach, the accuracy of such systems is limited by artifacts generated by non-uniform gel matrices and other factors. Such automated systems are generally riot equipped to accurately process the effects of such artifacts, which are typically manifested as "smiling" compressions, faint ghost bands, and the like. Manual interpretation of such results are therefore often required which significantly increases analysis time.

Researchers have, within the past several years, recognized a need for more rapid and sensitive techniques for analyzing the structure and sequences of biomolecules. Mass spectrometry (MS) techniques, such as time-of-flight mass spectrometry (TOFMS) and Fourier Transform ion-cyclotron-resonance mass spectroscopy, are well known techniques for quickly and accurately providing ion mass information from which sequence and structural determinations can be made. As is known in the art, TOFMS systems accelerate ions, via an electric field, toward a field-free flight tube which terminates at an ion detector. In accordance with known TOFMS principles, ion flight time is a function of ion mass so that ions having less mass arrive at the detector more quickly than those having greater mass. Ion mass can thus be computed from ion flight time through the instrument. FIG. 1 demonstrates this principle for a cytochrome-c sample, having a known mass to charge ratio (m/z) of 12,360 da, and a lysozyme sample, having a known mass to charge ratio (m/z) of 14,306 da. In FIG. 1, signal peak 10, having a flight time of approximately 40.52 $\mu s$ corresponds to the lighter cytochrome-c sample, and signal peak 12, having a flight time of approximately 41.04 $\mu s$, corresponds to the heavier lysozyme sample.

Due to the significantly decreased sample preparation and analysis times of MS techniques over the above-described PAGE technique, several MS sequencing strategies have recently been developed. Such MS sequencing techniques are generally operable to measure the change in mass of a biomolecule as residues are sequentially removed from its end. Examples of two such techniques, each involving elaborate pre-MS processing techniques, are described in U.S. Pat. Nos. 5,210,412 to Levis et al. and 5,622,824 to Köster.

In order to provide for the capability of determining sequence and structural information for large biomolecules, it has been recognized that MS techniques must accordingly be capable of generating large ions. Currently, at least two techniques are known for generating large ions for spectral analysis; namely electrospray ionization (ESI) and matrix assisted laser desorption ionization (MALDI). While both large ion generating techniques are readily available, known MS techniques are limited in both the quantity and quality of discernable information. Specifically, for large biomolecules, defined here as those containing at least 50 residues, mass spectra of parent and sequence related fragment ions become congested to the degree that mass (TOF) peaks overlap.

One solution to the problem of congested mass spectra is to increase the mass resolution capability of the MS instrument. Recent efforts at increasing such resolution have been successful, and complete sequence information for a 50 base pair DNA has been obtained using a Fourier Transform ion cyclotron resonance (FTICR) instrument. However, such instruments are extremely expensive, not readily available, and because of their extremely high vacuum requirements, they are generally not suitable for routinely sequencing large numbers of samples.

Another solution to the problem of congested mass spectra is to pre-separate the bulk of ions in time prior to supplying them to the ion acceleration region of the MS instrument. Mass spectrometry can then be performed sequentially on "packets" of separated ion samples, rather than simultaneously on the bulk of the generated ions. In this manner, mass spectral information provided by the MS instrument may be spread out in another dimension to thereby reduce the localized congestion of mass information associated with the bulk ion analysis.

One known ion separation technique which may be used to pre-separate the bulk of the ions in time prior to MS analysis is ion mobility spectrometry (IMS). As is known in the art, IMS instruments typically include a pressurized static buffer gas contained in a drift tube which defines a constant electric field from one end of the tube to the other. Gaseous ions entering the constant electric field area are accelerated thereby and experience repeated collisions with the buffer gas molecules as they travel through the drift tube. As a result of the repeated accelerations and collisions, each of the gaseous ions achieves a constant velocity through the drift tube. The ratio of ion velocity to the magnitude of the electric field defines an ion mobility, wherein the mobility of any given ion through a high pressure buffer gas is a function of the collision cross-section of the ion with the buffer gas and the charge of the ion. Generally, compact conformers, i.e. those having smaller collision cross-sectional areas, have higher mobilities, and hence higher velocities through the buffer gas, than diffuse conformers of the same mass, i.e. those having larger collision cross-sectional areas. Thus, ions having larger collision cross-sections move more slowly through the drift tube of an TMS instrument than those having smaller collision cross-sections, even though the ions having smaller collision cross-sections may have greater mass than those having higher collision cross-sections. This concept is illustrated in FIG. 2 which shows drift times through a conventional IMS instrument for three ions, each having a different mass and shape (collision cross-section). As is evident from FIG. 2, the most compact ion 14 (which appears to have the greatest mass) has the shortest drift time peak 16 of approximately 5.0 ms, the most diffuse ion 18 has the longest drift time peak 20 of approximately 7.4 ms, and the ion 22 having a collision cross-section between that of ion 14 and ion 18 (which also appears to have the least mass), has a drift time peak 24 of approximately 6.1 ms.

Referring now to FIG. 3, an ion time-of-flight spectrum 26, obtained from a known time-of-flight mass spectrometer, is shown plotted vs ion drift time. In this figure, ions of different mass are dispersed over different times of flight in the mass spectrometer. However, due to the limited resolution of the mass spectrometer, ions are not completely separated in the spectrum, i.e. dots corresponding to different ions overlap. When compared with FIG. 6, which will be discussed more fully in the DESCRIPTION OF THE PREFERRED EMBODIMENTS section, it is evident that different ions can be better resolved by an instrument that separates ions in two dimensions, namely ion mobility and ion mass.

Guevremont et al. have recently modified an existing IMS/MS instrument to convert the quadrupole MS to a TOFMS [R. Guevremont, K. W. M. Siu, and L. Ding, PROCEEDINGS OF THE 44TH ASMS CONFERENCE, (1996), Abstract]. Ions are generated in the Guevremont et al. instrument via electrospray, and 5 ms packets are gated into the IMS instrument, The ion packets produced by the IMS instrument are passed through a small opening into an ion acceleration region of the TOFMS.

While Guevremont et al. have had some experimental success in coupling an IMS instrument to a TOFMS instrument, their resulting instrumentation and techniques have several drawbacks associated therewith. For example, since the Guevremont et al. abstract discusses using 5 ms gate pulses to admit ions into the IMS instrument, it is noted that the resultant IMS spectrum has low resolution with at least 5 ms peak widths. Secondly, because the drift tube and ion flight tube of the Guevremont et al. instrument are colinear, any spatial and temporal spread in an ion packet leaving the IMS leads directly to a spatial and temporal spread of ions in the ion acceleration region of the TOFMS. These two characteristics lead to poor mass resolution in the TOFMS. The combination of low resolution in the IMS and low resolution in the TOFMS makes this instrument incapable of resolving complex mixtures. What is therefore needed is a hybrid IMS/TOFMS instrument optimized to resolve complex mixtures. Such an instrument should ideally provide for optimization of the ion mobility spectrum as well as optimization of the mass spectrum. Moreover, such a system should provide for an optimum interface between the two instruments to thereby maximize the capabilities of the TOFMS.

SUMMARY OF THE INVENTION

The foregoing drawbacks associated with the prior art system discussed in the BACKGROUND section are addressed by the present invention. In accordance with one aspect of the present invention, a method of generating ion mass spectral information comprises the steps of generating a gaseous bulk of ions, separating the gaseous bulk of ions in time along a first axis to form a number of ion packets each having a unique ion mobility associated therewith, sequentially separating at least some of the ion packets in time along a second axis perpendicular to the first axis to form a number of ion subpackets each having a unique ion mass associated therewith, and processing at least some of the ion subpackets to determine mass spectral information therefrom. One preferred apparatus for carrying out the foregoing method comprises means for generating a gaseous bulk of ions from a sample source, an ion mobility spectrometer (IMS) defining an ion inlet opening at one end thereof in fluid communication with the means for generating a gaseous bulk of ions and an ion out let opening at an opposite end thereof, wherein the ion inlet and outlet openings define a first axis therebetween, and a time-of-flight mass spectrometer (TOFMS) defining an ion acceleration region at one end thereof in fluid communication with the ion outlet opening and an ion detector at an opposite end thereof, wherein the ion acceleration region and the ion detector define a second axis therebetween perpendicular to the first axis.

In accordance with another aspect of the present invention, a method of generating ion mass spectral information comprises the steps of generating a gaseous bulk of ions, separating the gaseous bulk of ions in time along a first axis to form a number of ion packets each having a unique ion mobility associated therewith, sequentially collecting the ion packets in, and ejecting ion packets from, a first ion trap, sequentially separating in time at least some of the ion packets ejected from the first ion trap along a second axis to form a number of ion subpackets each having a unique ion mass associated therewith, and processing at least some of the ion subpackets to determine mass spectral information therefrom. One preferred apparatus for carrying out the foregoing method comprises means for generating a gaseous bulk of ions from a sample source, an ion mobility spectrometer (IMS) defining an ion inlet opening at one end thereof in fluid communication with the means for generating a gaseous bulk of ions and an ion outlet opening at an opposite end thereof, wherein the ion inlet and outlet openings define a first axis therebetween, an ion trap defining an ion inlet in fluid communication with the ion outlet opening of the IMS and an ion outlet, and a mass spectrometer (MS) defining an ion acceleration region at one end thereof in fluid communication with the ion outlet of the ion trap and an ion detector at an opposite end thereof, wherein the ion acceleration region and the ion detector define a second axis therebetween.

In accordance with yet another embodiment of the present invention, a method of generating ion mass spectral information comprises the steps of generating gaseous ions from a sample source, collecting at least some of the generated ions in an ion trap, repeating the generating and collecting steps a number of times to thereby form a gaseous bulk of ions in the ion trap, releasing the gaseous bulk of ions from the ion trap, separating the gaseous bulk of ions in time along a first axis to form a number of ion packets each having a unique ion mobility associated therewith, sequentially separating in time at least some of the ion packets along a second axis to form a number of ion subpackets each having a unique ion mass associated therewith, and processing at least some of the ion subpackets to determine mass spectral information therefrom. One preferred apparatus for carrying out the foregoing method comprises means for generating a gaseous bulk of ions from a sample source, a first ion trap defining an ion inlet in fluid communication with the means for generating a gaseous bulk of ions and an ion outlet, an ion mobility spectrometer (IMS) defining an ion inlet opening at one end thereof in fluid communication with the ion outlet of the first ion trap and an ion outlet opening at an opposite end thereof, wherein the ion inlet and outlet openings define a first axis therebetween, and a mass spectrometer (MS) defining an ion acceleration region at one end thereof in fluid communication with the ion outlet opening of the IMS and an ion detector at an opposite end thereof, wherein the ion acceleration region and the ion detector define a second axis therebetween.

One object of the present invention is to provide instrumentation for rapid analysis and sequencing of large biomolecules, as well as analysis of mixtures of organic and inorganic molecules.

Another object of the present invention is to provide a hybrid ion mobility and time-of-flight spectrometer for composition, sequence and structural analysis of biomolecules.

Yet another object of the present invention is to optimize such an instrument for sensitivity and resolution of both ion mobility and ion mass spectra.

These and other objects of the present invention will become more apparent from the following description of the preferred embodiments.

DESCRIPTION OF THE PREFERRED EMBODIMENTS

Figure 1:
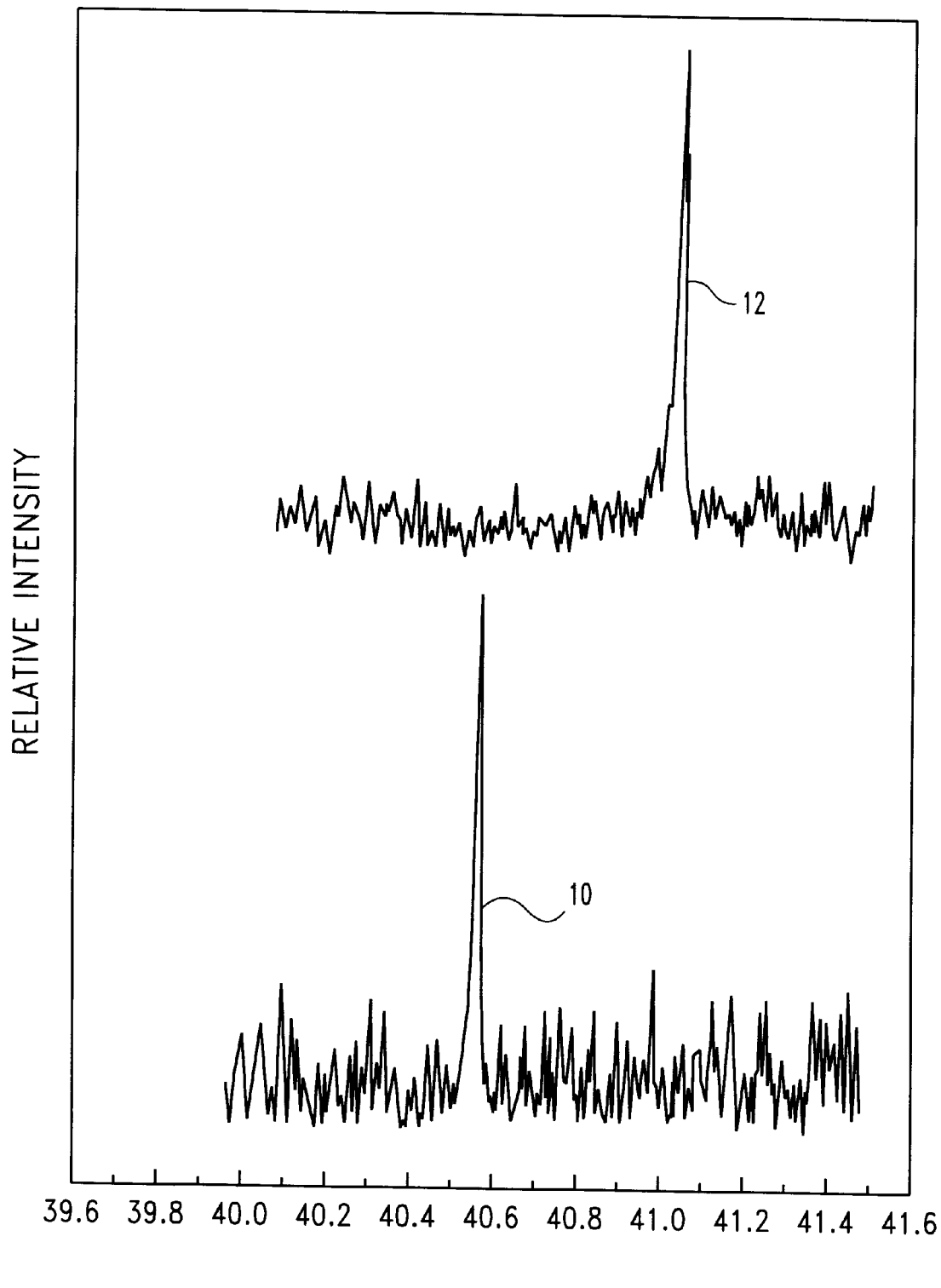
FIG. 1 is a MALDI-TOF mass spectrum of cytochrome-c and lysozyme.
Figure 2:
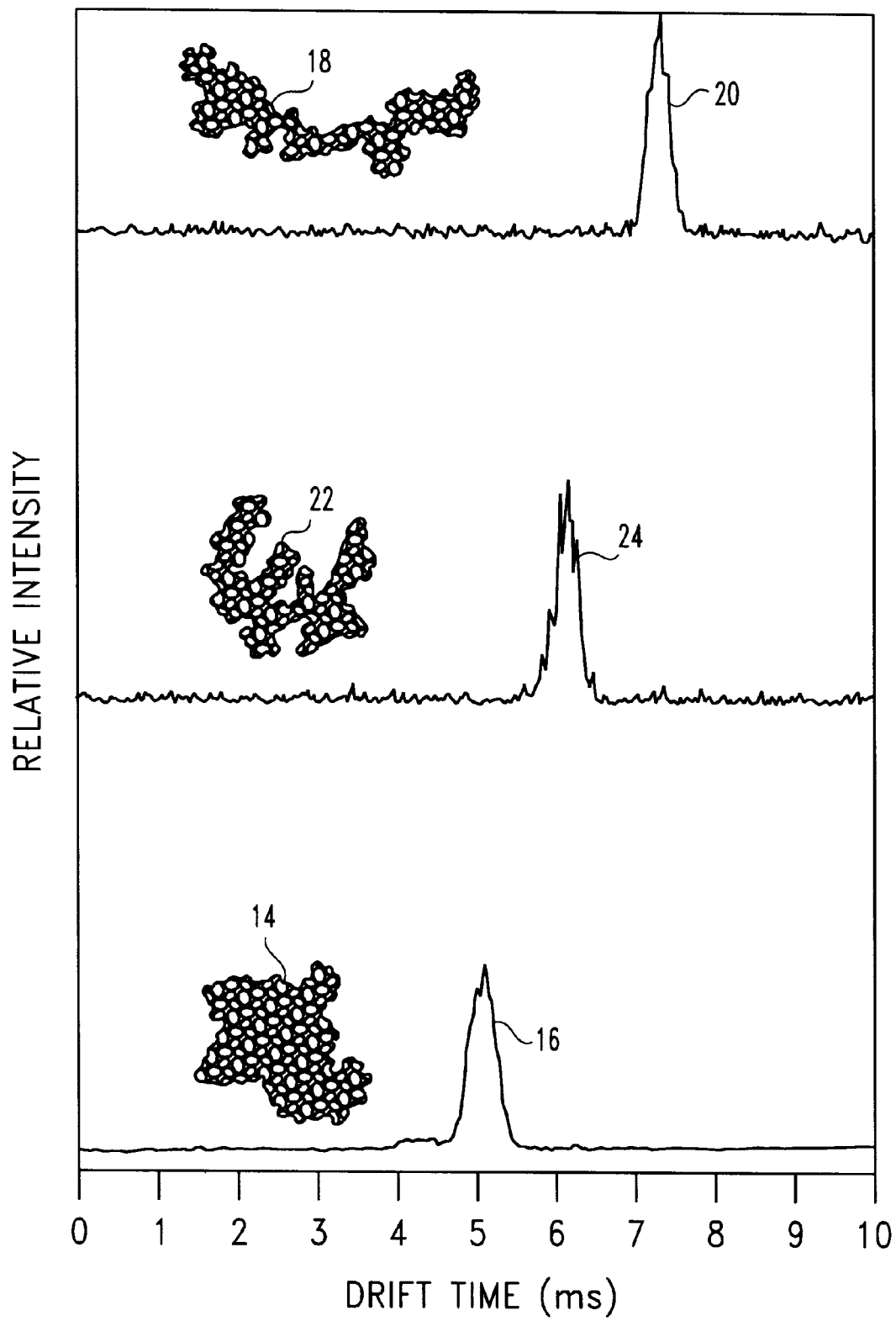
FIG. 2 is an IMS drift time distribution for three ions having different collision cross-sections.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Figure 4:
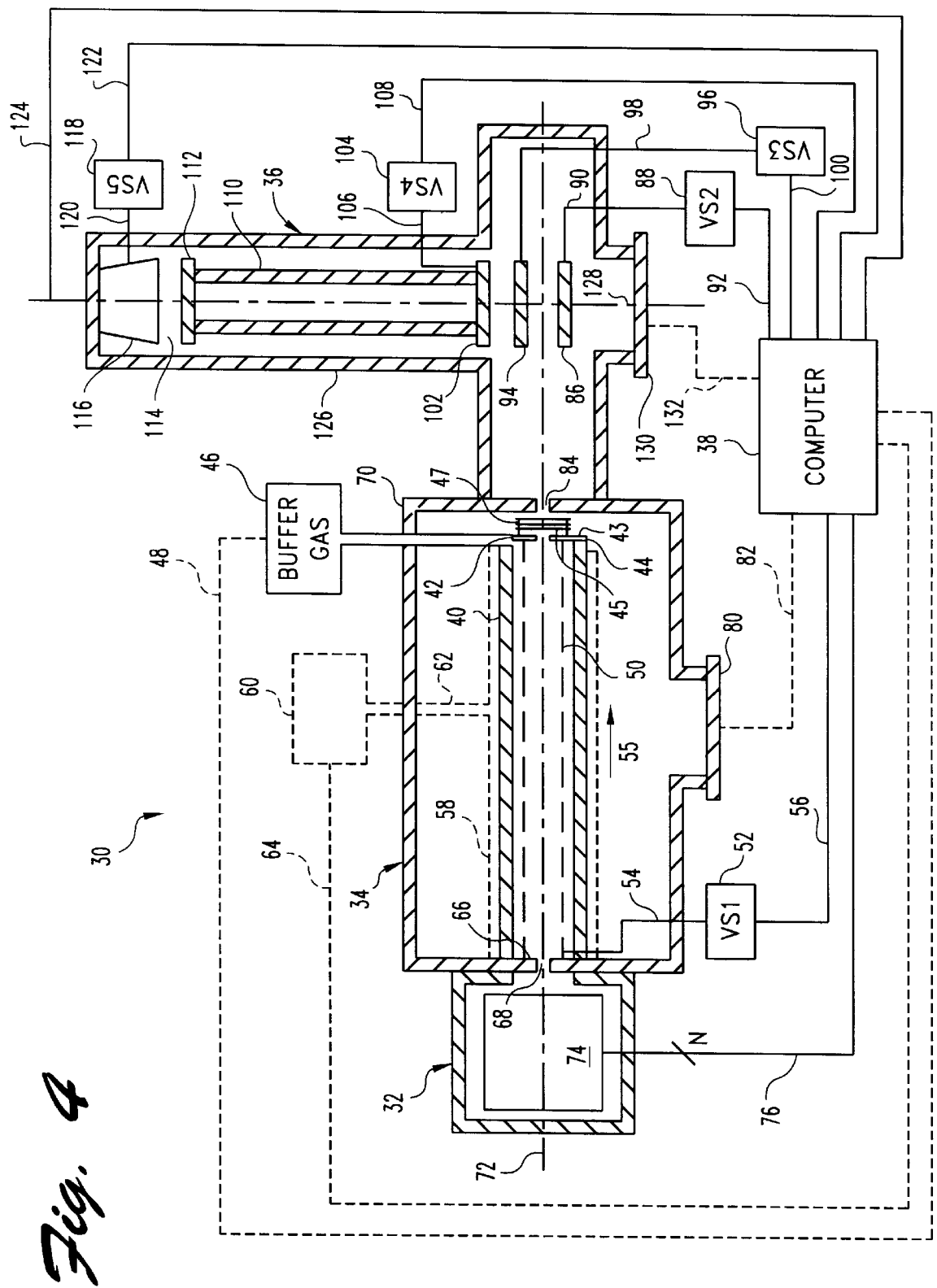
FIG. 4 is a cross-section and schematic diagram of one embodiment of a hybrid ion mobility and time-of-flight mass spectrometer, in accordance with the present invention.

Referring now to FIG. 4, one preferred embodiment of a hybrid ion mobility and time-of-flight mass spectrometer instrument 30, in accordance with the present invention, is shown. Instrument 30 includes, as its basic components, an ion source region 32 in communication with an ion mobility spectrometer 34, which itself is in communication with a mass spectrometer 36. A computer 38 is provided for controlling at least some portions of the instrument 30 as well as for collecting ion information from mass spectrometer 36. Computer 38 is preferably a personal computer (PC) of known construction having at least a known 386 processor, although the present invention contemplates that computer 38 may be any known computer, controller or data processor capable of controlling instrument 30, as set forth in greater detail hereinafter, and of collecting and processing ion information from mass spectrometer 36.

Preferably, mass spectrometer 36 is of the linear time-of-flight type, although the present invention contemplates that spectrometer 36 may alternatively be a known reflectron time of flight mass spectrometer or Fourier Transform ion-cyclotron-resonance (FTICR-MS) mass spectrometer. In one preferred embodiment, the TOFMS 36 is configured to maximize mass resolution by minimizing the deleterious effects of initial ion position and initial ion velocity distributions. Details of such a TOFMS configuration and operation thereof are given in U.S. Pat. Nos. 5,504,326 and 5,510,613 to Reilly et al., assigned to the assignee of the present invention, the contents of which are incorporated herein by reference.

Ion mobility spectrometer (IMS) 34 includes a drift tube 40 having a gas port 42 disposed adjacent an ion exit end 44 of tube 40, wherein port 42 is connected to a source of buffer gas 46. The flow rate of buffer gas may be controlled by computer 38 via signal path 48, or may alternatively be controlled by a manually actuated valve (not shown). Ion exit end 44 of drift tube 40 includes an endplate 43 attached thereto, wherein endplate 43 defines an opening, or ion aperture, 45 therethrough.

Drift tube 40 includes a number of guard rings 50 distributed along its inner surface, wherein the guard rings 50 are interconnected by equivalent-valued resistors (not shown). The guard ring positioned most adjacent to ion source region 32 is connected to a voltage source VS1 52 via signal path 54, and source 52 is preferably controlled by computer 38 via signal path 56, although the present invention contemplates controlling source 52 via a manual actuator (not shown). The drift tube 40 defines a longitudinal axis 72 therethrough which will be referred to hereinafter as the drift tube axis 72. Voltage source 52 is preferably set to a positive voltage to thereby establish a constant electric field directed along axis 72 in a direction indicated by arrow 55. Those skilled in the art will recognize that the importance of the guard ring and voltage source arrangement of spectrometer 34 lies not in its specific structure, but in its ability to establish, as accurately as possible, a constant electric field in the direction of arrow 55. In this sense, the present invention contemplates that any known structure or arrangement may be used to establish such an electric field within drift tube 40 in the direction of arrow 55. It is to be understood, however, that a constant electric field in the direction of arrow 55 is established to accelerate positively charged ions toward tube end 44, and that such an electric field may be reversed to thereby accelerate negatively charged ions toward tube end 44.

Drift tube 40 may optionally be surrounded by a variable temperature housing 58 which is connected to a variable temperature source 60 via path 62, all of which are shown in phantom. In one embodiment, variable temperature source 60 is a fluid holding tank and path 62 is a conduit leading to housing 58 which, in this case, is preferably sealed. A return conduit (not shown) is also connected to the fluid holding tank so that fluid from within the tank may be circulated through housing 58. The fluid within the fluid holding tank may be a heated or cooled gas or liquid such as, for example, liquid nitrogen. In an alternate embodiment, variable temperature source 60 is a known electrically actuatable temperature controller, and path 62 comprises a pair of electrical conductors connected between the controller and housing 58. In operation, temperature controller is operable to heat or cool housing 58 as desired. Regardless of the particular embodiment of housing 58, source 62 and path 62, the present invention contemplates that source 60 may furthermore be controlled by computer 38 via signal path 64.

Drift tube 40 is further surrounded by a housing 70 which defines a tube end 66 covering an ion entrance end thereof, wherein tube end 66 defines an opening, or ion aperture, 68 therethrough, and an ion exit opening, or aperture, 84 adjacent to endplate 43. Preferably, ion optics 47 are positioned between openings 45 and 84 to focus ions exiting opening 45 into an ion acceleration region of TOFMS 36. Openings 45, 68 and 84 are preferably bisected by drift tube axis 72. An ion source 74, which will be described more fully hereinafter, is positioned within ion source region 32 and is operable, preferably under the control of computer 38 via a number, N, of signal paths 76, wherein N may be any positive integer, to direct ions within the spectrometer 34 via opening 68. Ions entering drift tube 40 separate in time as a function of their individual mobilities, as discussed hereinabove, and are sequentially directed through opening 70 toward TOFMS 36.

Housing 70 includes d pump 80 for controlling the pressure of the buffer gas. Preferably, pump 80 is a diffusion pump, the operation of which may be controlled by computer 38 via signal path 82. Alternatively, pump may be manually controlled by a manual pump actuator (not shown). In any case, pump 80 is operable to establish a desired pressure of the static buffer gas within drift tube 40. In accordance with known TMS techniques, the buffer gas within drift tube 40 may typically be set within the range of between approximately one and a few thousand Torr.

TOMS 36 is preferably surrounded by a housing 126 that is attached to IMS 34. TOFMS 36 includes a first electrically conductive grid or plate 86 connected to a second voltage source VS2 88 via signal path 90, which is preferably controlled by computer 38 via signal path 92. A second electrically conductive grid or plate 94 is connected to a third voltage source VS3 96 via signal path 98, which is preferably controlled by computer 38 via signal path 100. A third electrically conductive grid or plate 102 is connected to a fourth voltage source VS4 via signal path 106, which is preferably controlled by computer 38 via signal path 108. Grids or plates 86, 94 and 102 define first and second ion acceleration regions therebetween as is known in the art, and which will be more fully described hereinafter. Those skilled in the art will recognize that other known ion acceleration region structures may be used with TOFMS 36, such as, for example, positioning a fourth grid or plate between grids or plates 94 and 102.

Grid or plate 102 has a plate surface attached to one end of a flight tube 110, the opposite end of which is attached to a surface of a fourth electrically conductive grid or plate 112. An ion detector 116 is disposed adjacent to grid or plate 112 with an air gap 114 defined therebetween. Ion detector 116 is connected to a fifth voltage source VS5 118 via signal path 120, which is preferably controlled by computer 38 via signal path 122. Ion detector 116 further has a signal output connected to computer 38 via signal path 124, whereby detector 116 is operable to provide ion arrival time information to computer 38. Grids or plates 86, 94, 102 and 112 are preferably arranged in juxtaposition with each other such that all plate surfaces having greatest surface area are parallel with each other, as well as to the surface of the ion detector 116, and are further preferably perpendicular to a longitudinal axis 128 defined centrally through the flight tube 110, which will hereinafter be referred to as the flight tube axis 128.

TOFMS 36 further includes a pump 130 for controlling the vacuum of the TOFMS chamber defined by housing 126. Preferably, pump 130 is a diffusion pump, the operation of which may be controlled by computer 38 via signal path 132. Alternatively, pump may be manually controlled by a manual pump actuator (not shown). In any case, pump 130 is operable to establish a desired vacuum within housing 126 which may be set, in accordance with known TOFMS operating techniques, to within the range of between approximately $10^{-4}$ and $10^{-10}$ Torr.

In the instrument 30 illustrated in FIG. 4, TOFMS 36 is preferably arranged relative to IMS 34 such that the flight tube axis 128 is perpendicular to the drift tube axis 72. Moreover, TOFMS 36 is preferably positioned relative to IMS 34 such that the drift tube axis 72 and the flight tube axis 128 bisect within the first ion acceleration region defined between grids or plates 86 and 94. In an alternative configuration of TOFMS 36, grid or plate 94 may be omitted, and the TOFMS 36 need then be positioned relative to IMS 34 such teat the drift tube axis 72 bisects the flight tube axis 128 within the ion acceleration region defined between grids or places 86 and 102. In either case, TOFMS is preferably positioned relative to IMS 34 such that the drift tube axis 72 bisects the flight tube axis 128 approximately centrally within the region of interest.

In the operation of instrument 30, ions are generated by ion source 74, in accordance with one or more ion generation techniques described hereinafter, and are supplied to IMS 34 via IMS inlet opening 68. A buffer gas typically used in IMS instruments 34 is supplied to drift tube 40 via buffer gas source 46, wherein the buffer gas is regulated to a desired pressure via pump 80, buffer gas source 46 or a combination thereof. Typically, the buffer gas is regulated to a pressure of between approximately 1 and a few thousand Torr. Voltage source 52 supplies a voltage sufficient to generate a constant electric field along the drift tube axis in a direction indicated by arrow 55.

In accordance with known IMS 34 operation, ions entering IMS inlet opening 68 travel through drift tube 40 toward IMS outlet opening 84, wherein the ions separate in time according to their individual mobilities. Ions having low mobility lag behind those having higher mobility, wherein ion mobilities are largely a function of their collision cross-sections. As a result, the more compact ions arrive at the IMS outlet opening 84 more quickly than diffuse ions. Those skilled in the art will recognize that the temperature of drift tube 40 may also be controlled via variable temperature source 60 so that ion mobility analysis may be performed as a function of temperature.

TOFMS 36 is operable to accelerate ions from the space defined between grids or plates 86 and 94 toward a field-free flight tube 110, wherein the ions separate in time according to their individual masses. Generally, ions having less mass will reach the detector 116 more quickly than those having greater mass. The detector 116 is operable to detect arrival times of the ions thereat and provide signals corresponding thereto to computer 38 via signal path 124.

As set forth in greater detail in U.S. Pat. Nos. 5,504,26 and 5,510,613 to Reilly et al., which have been incorporated herein by reference, voltage sources VS2 88, VS3 96 and VS4 104 are typically controlled by computer 38 to initially establish voltages at grids or plates 86, 94 and 102 that match the voltage level associated with IMS 34 (which is set by voltage source VS1 52). Depending upon various instrument parameters, such as the length of flight tube 110, the distances between grids or plates 88, 94, 102 and 112, and the distance 114 between grid or plate 112 and detector 116, as well as estimates of initial ion position or initial ion velocity within the space defined between grids or plates 86 and 94, computer 38 is operable to control sources 88, 96 and/or 104 to instantaneously increase the electric field between grids or plates 86, 94 and 102 to thereby create an ion drawout electric field therebetween which accelerates ions between these grids toward flight tube 110. Preferably, the pulsed ion drawout electric field is in a direction from grid or plate 86 toward flight tube 110 to thereby accelerate positively charged ions toward the flight tube 110. Those skilled in the art will recognize, however, that this electric field may alternatively be reversed to accelerate negatively charged ions toward the flight tube 110.

In any event, ions within the space defined between grids or plates 86 and 94 are accelerated by the pulsed ion drawout electric field to the space defined between grids or plates 94 and 102. Due to the fact that ions entering the region defined between grids or plates 86 and 94 along axis 72 have a narrow spatial distribution, due to focusing of the ions into this region via ion optics 47, and a small velocity component along axis 128, it is possible to choose the pulsed voltage applied to grids or plates 86 and/or 94 in such a way as to obtain sharp TOFMS peaks. The goal of the pulsed ion drawout electric field and the subsequent acceleration of the ions between grids or plates 94 and 102 is to provide all ions reaching grid or plate 102 with substantially the same kinetic energy. The flight tube 110 has no electric field associated therewith so that the ions drift from grid or plate 102 toward detector 116, wherein the ions separate in time as a function of their individual masses as described hereinabove. Computer 38 typically controls voltage source VS5 118 to supply a voltage thereto during detection times to thereby increase the gain of detector 116 as is known in the art.

Pump 130 controls the vacuum within TOFMS 36, and pump 130 is preferably controlled by computer 38 via signal path 132. TOFMS 36 is typically operated between $10^{-4}$ and $10^{-10}$ Torr.

In the embodiment 30 of the hybrid IMS/TOFMS instrument illustrated in FIG. 4, drift tube axis 72 preferably bisects the space defined between grids or plates 86 and 94 of TOFMS 36, and is perpendicular to flight tube axis 128. The present invention alternatively contemplates arranging TOFMS 36 relative to IMS 34 such that the drift tube axis 72 passes between grids or plates 86 and 94 perpendicular to flight tube axis 128, but at some other known distance relative to either of the grids or plates 86 and 94. In either case, the foregoing structural positioning of TOFMS 36 relative to IMS 34 provides advantages over non-perpendicular arrangements of the draft tube axis 72 relative to the flight tube axis 128. For example, such a perpendicular arrangement ensures that ion packets entering the ion acceleration region defined between grids or plates 86 and 94 from IMS 34 will have constant and relatively well defined initial ion positions as they travel therebetween along axis 72. As discussed briefly hereinabove, ion optics 47 focus ions into the ion acceleration region to thereby minimize spatial distribution of the ions. Moreover, since axis 72 is parallel with grids or plates 86 and 94, ion position with respect to axis 128 will remain relatively constant. This feature provides for the ability to accurately estimate initial ion position within the ion acceleration region defined between grids or plates 86 and 94, to thereby allow a more accurate estimation of the pulsed ion drawout electric field discussed above.

Preferably, computer 38 controls the generation of ions from ion source 74 as will be discussed in greater detail hereinafter, so that computer 38 has knowledge of the times at which ions were introduced into IMS 34, hereinafter referred to as ion introduction events. The computer 38 is then operable to control voltage sources 88 and 96 to repeatedly provide the pulsed ion drawout field some number of times for every ion introduction event. In one embodiment, a pulsed ion drawout field is repeatedly provided 512 times for every ion introduction event. Those skilled in the art will recognize that the number of pulsed ion drawout fields provided for every ion introduction event is directly proportional to the ultimate resolution of the instrument 30. As this pulsed operation relates to some of the advantages of the perpendicular positioning of TOFMS 36 relative to IMS 34, such an arrangement minimizes the possibility that all or part of any one ion packet will travel through the TOFMS 36 unprocessed thereby. Due to the direction of travel of the ion packets relative to the grids or plates 86 and 94, and also to the pulsed nature of the ion drawout electric field, the TOFMS 36 will have multiple chances to accelerate each ion packet toward detector 116 as they travel along axis 72. As such, the instrument 30 is configured to provide for maximum ion throughput to detector 116.

Figure 5:
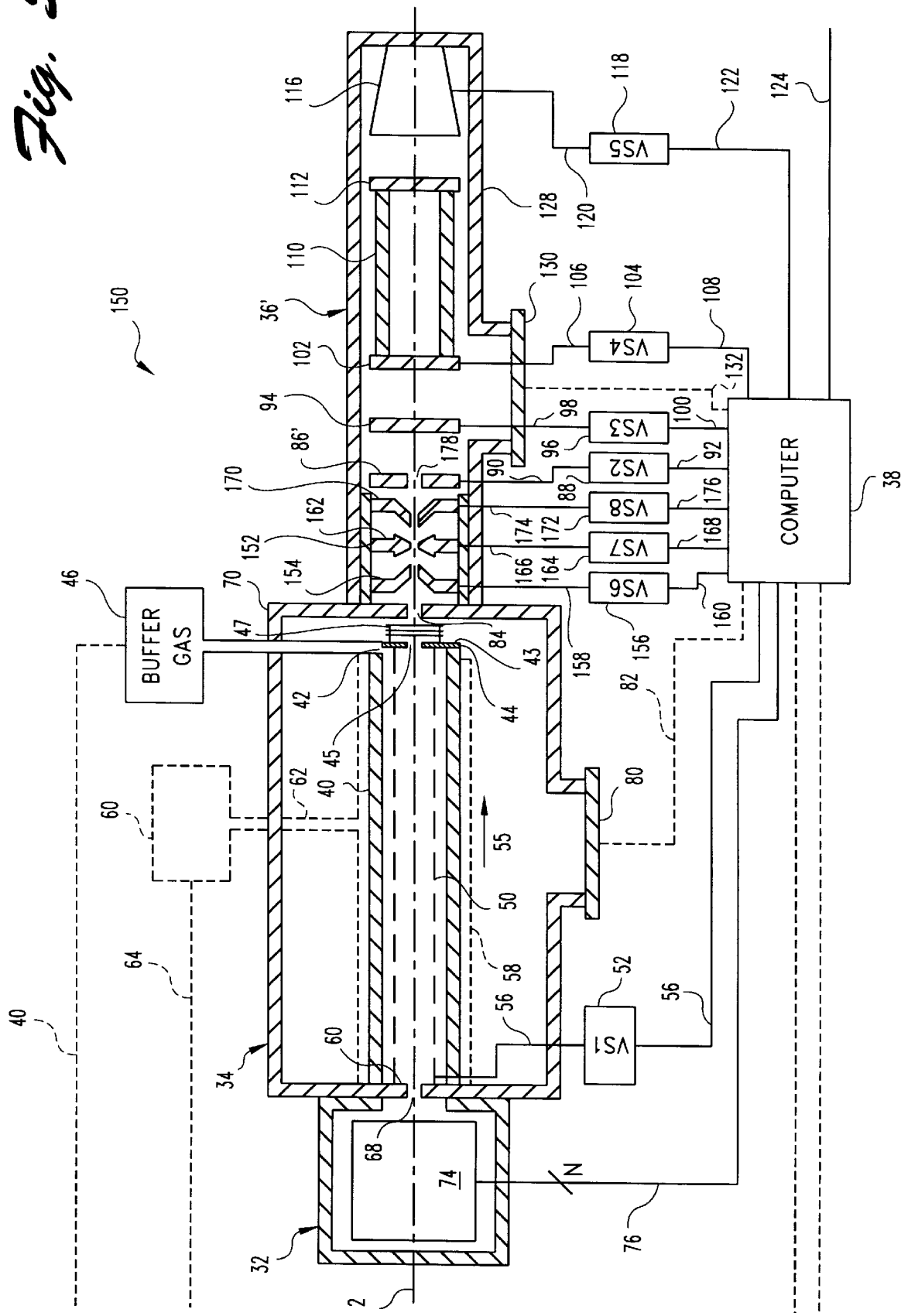
FIG. 5 is a cross-section and schematic diagram of an alternate embodiment of a hybrid ion mobility and time-of-flight mass spectrometer, according to the present invention.

Referring now to FIG. 5, an alternate embodiment of a hybrid ion mobility and time-of-flight mass spectrometer 150, in accordance with the present invention, is shown. Spectrometer 150 is similar in many respects to spectrometer 30 shown in FIG. 4 and described hereinabove, and like components are therefore identified with like numbers. Discussion of the common components, as well as the basic operation of IMS 34 and TOFMS 36', will therefore not be repeated for brevity's sake.

Unlike instrument 30 of FIG. 4, the TOFMS 36' of instrument 150 is positioned relative to IMS 34 such that the drift tube axis 72 also defines the flight tube axis of TOFMS 36'. Alternatively, TOFMS 36' could be arranged relative to IMS 34 with any orientation such that the drift tube axis 72 is non-perpendicular to the flight tube axis. In any such orientation, the initial positions of the ion packets within the space defined between grids or plates 86' and 94 either cannot be estimated with any degree of accuracy (as in the orientation illustrated) or changes as the ion packets travel along axis 72 (as in any non-perpendicular arrangement). Moreover, in any such orientation, it is difficult to estimate when, relative to an ion introduction event, the ion packets will arrive within the space defined between grids or plates 86' and 94, and the timing of the pulsed ion drawout electric fields is thus difficult to predict. As a result, it is likely that the timing of the pulsed ion drawout electric fields will be inaccurate so that ions may be lost within the TOFMS 36' and/or the mass resolution of the TOFMS 36' will be adversely affected.

In order to address the foregoing problems associated with non-perpendicular positioning of the TOFMS 36' relative to the IMS 34, which are the same problems associated with the Guevremont et al. system discussed hereinabove in the BACKGROUND section, instrument 150 is provided with an ion trap 152 operatively positioned between the ion outlet opening 84 of IMS 34 and the space defined between grids or plates 86' and 94. In the embodiment illustrated in FIG. 5, grid or plate 86' defines an ion inlet opening 178 therethrough which is aligned along axis 72 with ion outlet opening 84 of IMS 34. In other non-perpendicular arrangements of TOFMS 36' relative to IMS 34, ion inlet opening 178 may not be required since ions may enter the space between grids or plates 86' and 94 in the same manner as discussed with respect to the embodiment 30 illustrated in FIG. 4.

In any event, ion trap is preferably a known quadrupole ion trap having a first endcap 154, a center ring 162 and a second endcap 170. Each of the endcaps 154 and 170 define apertures therethrough which align with axis 72. In this configuration, ion trap 152 confines ions therein to a small volume in its center which is in alignment with the ion inlet opening to TOFMS 36'. First endcap is connected to a voltage source VS6 156 via signal path 158, which is itself connected to computer 38 via signal path 160. Center ring is connected to a voltage source VS7 164 via signal path 166, which is itself connected to computer 38 via signal path 168, and second endcap is connected to a voltage source VS8 172 via signal path 174, wherein source 172 is connected to computer 38 via signal path 176. Preferably, sources 156 and 172 are operable to produce dc voltages and source 164 is operable to produce ac voltages in the rf range.

In operation, computer 38 controls sources 156 and 172 to bias endcaps 154 and 170 such that ions exiting ion outlet opening 84 of IMS 34 have just enough energy to enter the opening defined in the first endcap 154. Once therein, the ions collide with buffer gas leaking out of opening 84 into the trap 152, and lose sufficient energy thereby so that the rf voltage on center ring 162 is operable to confine the ions within the trap 152. The confined ions undergo further collisions inside the trap 152 which causes the ions to correspondingly experience further energy loss, resulting in a concentration of the ions toward the center of ring 162 due to the rf voltage thereon. As long as the voltages on endcaps 152 and 170 and center ring 162 are maintained, ions may enter the trap 152 and collect therein. Ions are ejected out of the trap 152 by turning off the rf voltage on center ring 152 and applying an appropriate dc pulse to one of the endcaps 152 or 170. For example, to eject a collection of positively charged ions from trap 152, either the voltage on endcap 152 may be pulsed above that present on endcap 170 or the voltage on endcap 170 may be pulsed below that present on endcap 152. In general; the magnitude of the rf field applied to the center ring via source 164, as well as any dc voltage included therein, may be varied to thereby select ions of any desired mass to charge ratio to be collected by ion trap 152. Tons of all mass to charge ratios, or ions of any particular mass to charge ratio, may be selectively collected within ion trap 152 through proper choice of dc level and rf peak magnitude provided by voltage source 164.

As it relates to the present invention, the ion trap 152 is controllable by computer 38 to periodically eject the collected ion packets therefrom, hereinafter referred to as an ion ejection event, so as to provide for a more accurate estimate of initial ion position within the space defined between grids or plates 86' and 94. Since the computer 38 controls the time at which a packet of collected ions is ejected from ion trap 152, the time at which the ion packet arrives at a specified position in the space defined between grids or plates 86' and 94 can be accurately estimated. Knowing the approximate time, relative to the ion ejection event, at which the ion packet arrives at the specified position between grids or plates 86' and 94, computer 38 may more accurately estimate appropriate timing for applications of the pulsed ion drawout electric field to thereby provide for maximum mass resolution as discussed hereinabove. Moreover, providing for a more accurate estimate of the timing of the pulsed ion drawout electric fields reduces the likelihood that ion packets, or at least portions thereof, will be lost within the TOFMS 36'.

In the operation of instrument 150, IMS 34 is operable to provide packets of ions, which are separated in time as a function of ion mobility, to TOFMS 36' via ion outlet opening 84. Computer 38 controls ion trap 152 to collect the various ions packets therein one at a time, and eject each collected ion packet therefrom at periodic intervals. The ejected ions enter the space defined between grids or plates 86' and 94 as discussed hereinabove, and computer 38 is operable to compute appropriate times at which to apply the pulsed ion drawout electric fields based on the timing of the ion ejection events The TOFMS 36' is thereafter operable as described hereinabove to produce mass spectrum information.

Figure 3:
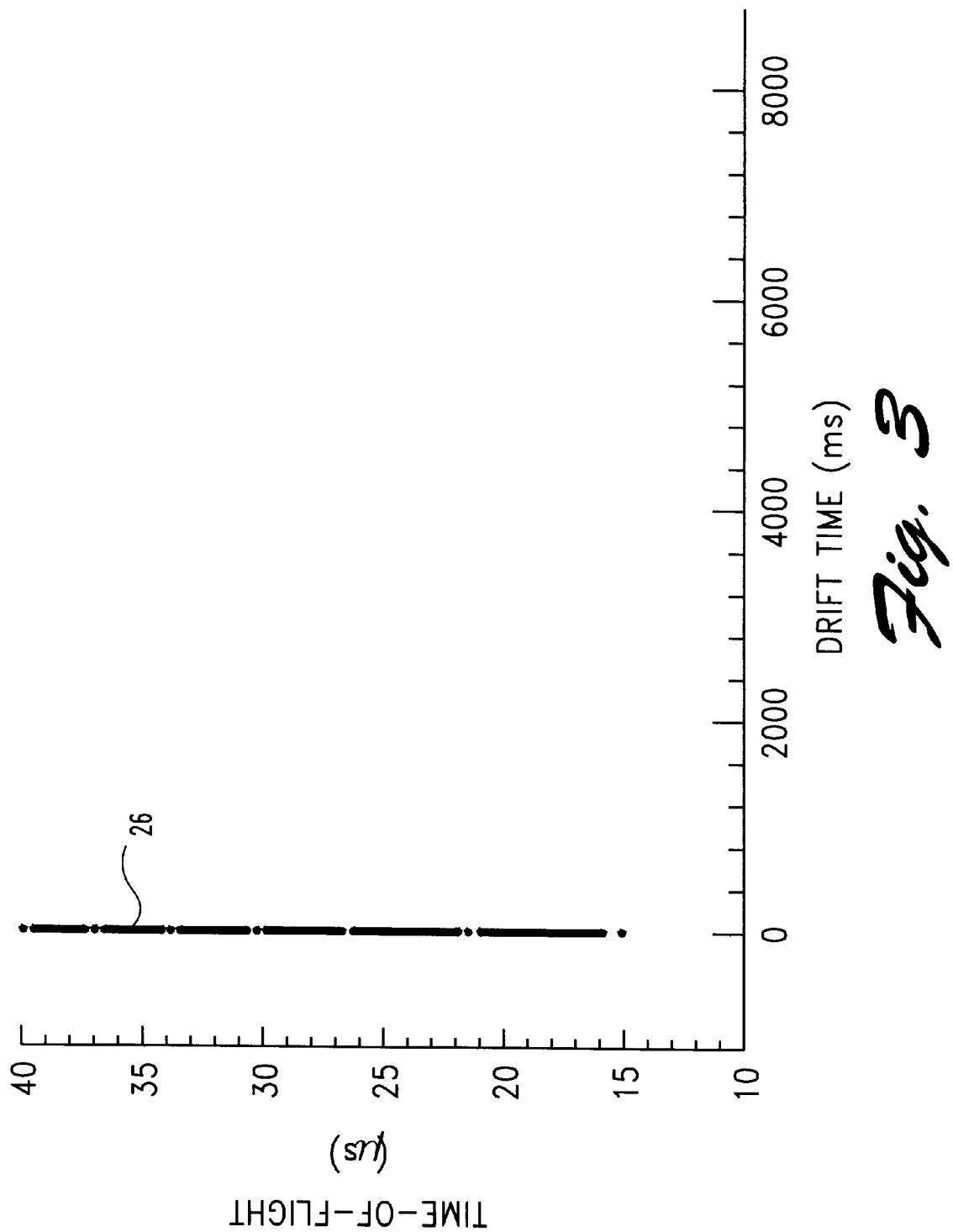
FIG. 3 is a mass spectrum plotted against drift time illustrating the limited resolution of a time-of-flight mass spectrometer.
Figure 6:
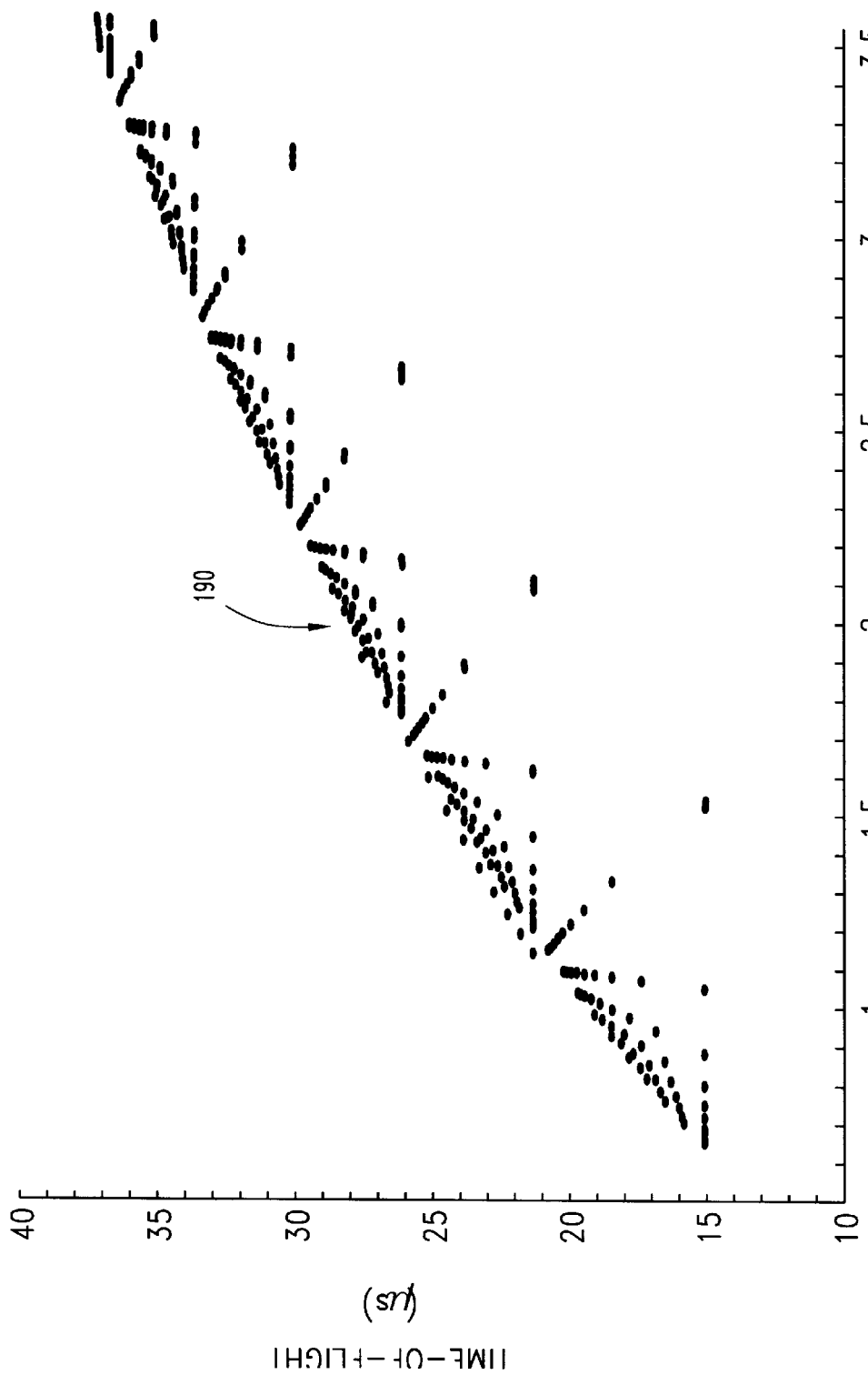
FIG. 6 is a plot of ion time-of-flight vs ion drift time for oligothymidine, utilizing the hybrid instrumentation of either FIG. 4 or FIG. 5.

Referring now to FIG. 6, a plot 190 of ion flight time vs ion draft time for an oligothymidine sample is shown, wherein the data shown is producible via either instrument embodiment 30 or 150. As compared to the plot of FIG. 3, it is apparent that the hybrid ion mobility and time-of-flight mass spectrometer of the present invention is operable to resolve structural information of molecules in two substantially orthogonal dimensions. For each drift time, corresponding to arrival in the TOFMS of a corresponding ion packet, the instrument of the present invention is operable to resolve a number of times-of-flight, corresponding to a number of mass to charge ratios. The plot 190 of FIG. 6 thus illustrates that the total resolving power of instrument 30 is drastically better than that achievable via an IMS or TOFMS alone. This technique dramatically reduces the problem of congestion of mass spectra, due to mass peak overlap, in obtaining sequence information for large biomolecules (in excess of 50 residues). The present invention thus provides an instrument for composition, sequence and structural analysis of biomolecules which does not suffer from drawbacks associated with prior art systems discussed in the BACKGROUND section.

Figure 7A:
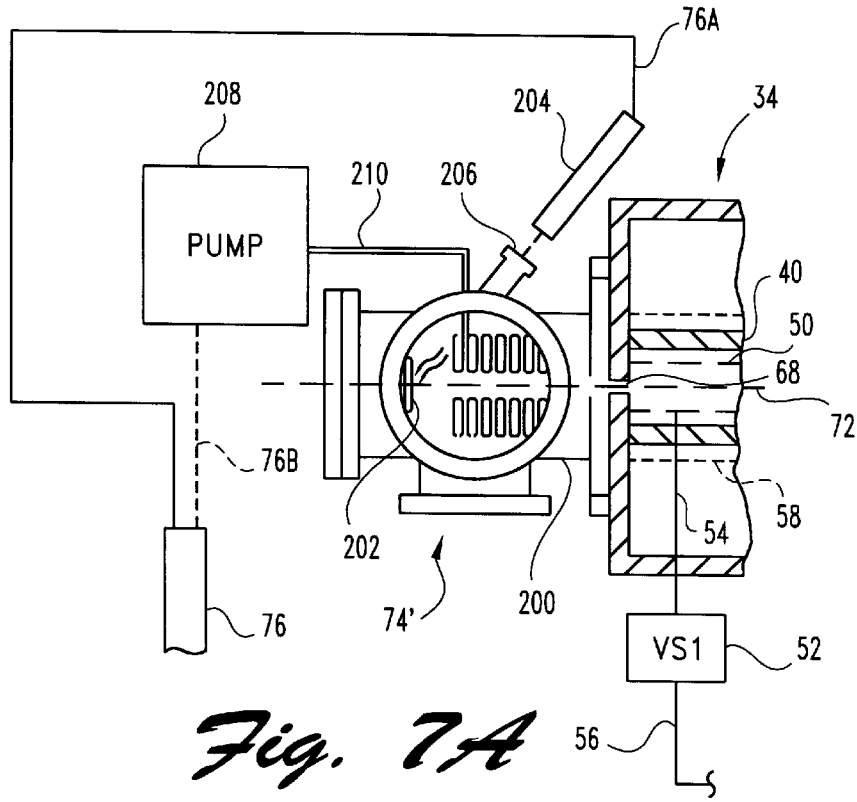
FIG. 7A is a diagrammatic illustration of one preferred embodiment of an ion source for use with either of the hybrid instruments shown in FIGS. 4 and 5.

Referring now to FIG. 7A, one preferred embodiment 74' of an ion source 74 for either of the instrument embodiments of FIGS. 4 and 5, is shown. Embodiment 74' includes a chamber 200 having a sample 202 mounted therein and an optical window 206 extending therefrom. A radiation source 204 is electrically connected to computer 38 via signal path 76A, and is configured to direct radiation through optical window 206 to thereby irradiate sample 202. Chamber 200 may include a conduit extending therefrom to a pump 208 which may be controlled by computer 38 via signal path 76B.

Ion source 74' is a known MALDI arrangement wherein radiation source 204, preferably a laser, is operable to desorb gaseous ions from a surface of the sample 202. Computer 38 is operable to control activation times of laser 204 to thereby control sample ionization events. The desorbed ions are directed by the internal structure of chamber 202 to ion inlet opening 68 of IMS 34. The sample 202 may, in accordance with the present invention, be a biomolecule of any size such as DNA, RNA, any of various proteins, carbohydrates, glycoconjugates, and the like. Pump 208 may be controlled to pressurize chamber 208 to thereby conduct high pressure MALDI analysis as is known in the art.

Figure 7C:
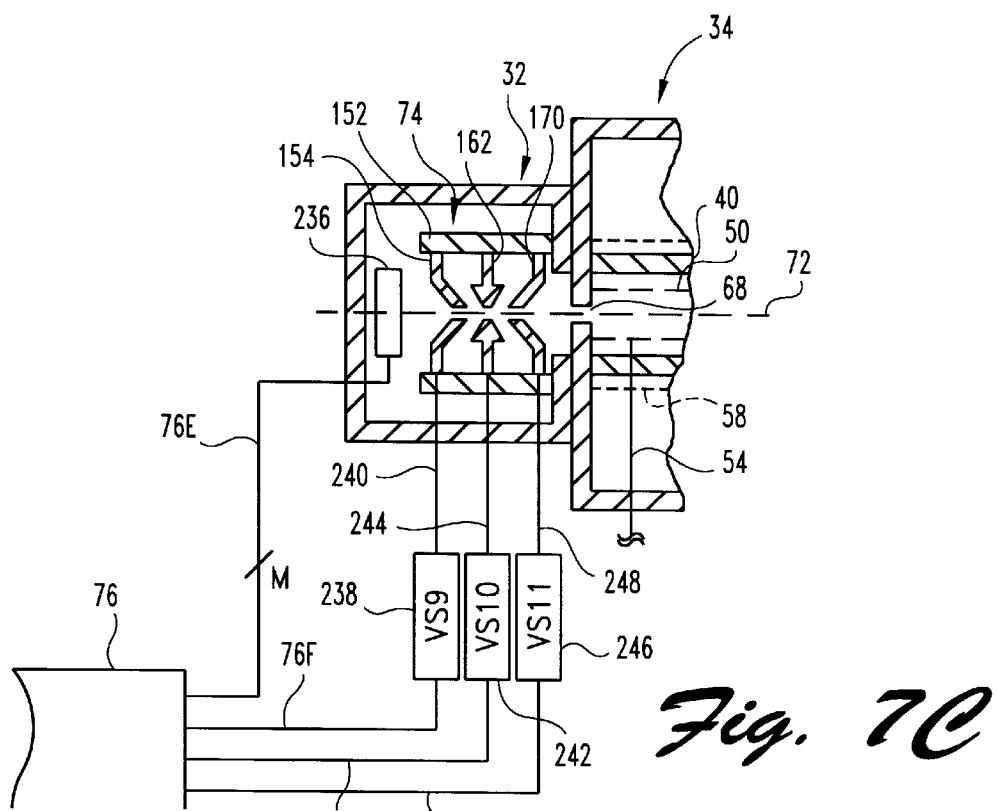
FIG. 7C is a diagrammatic illustration of another alternate embodiment of an ion source for use with either of the hybrid instruments shown in FIGS. 4 and 5.
Figure 7B:
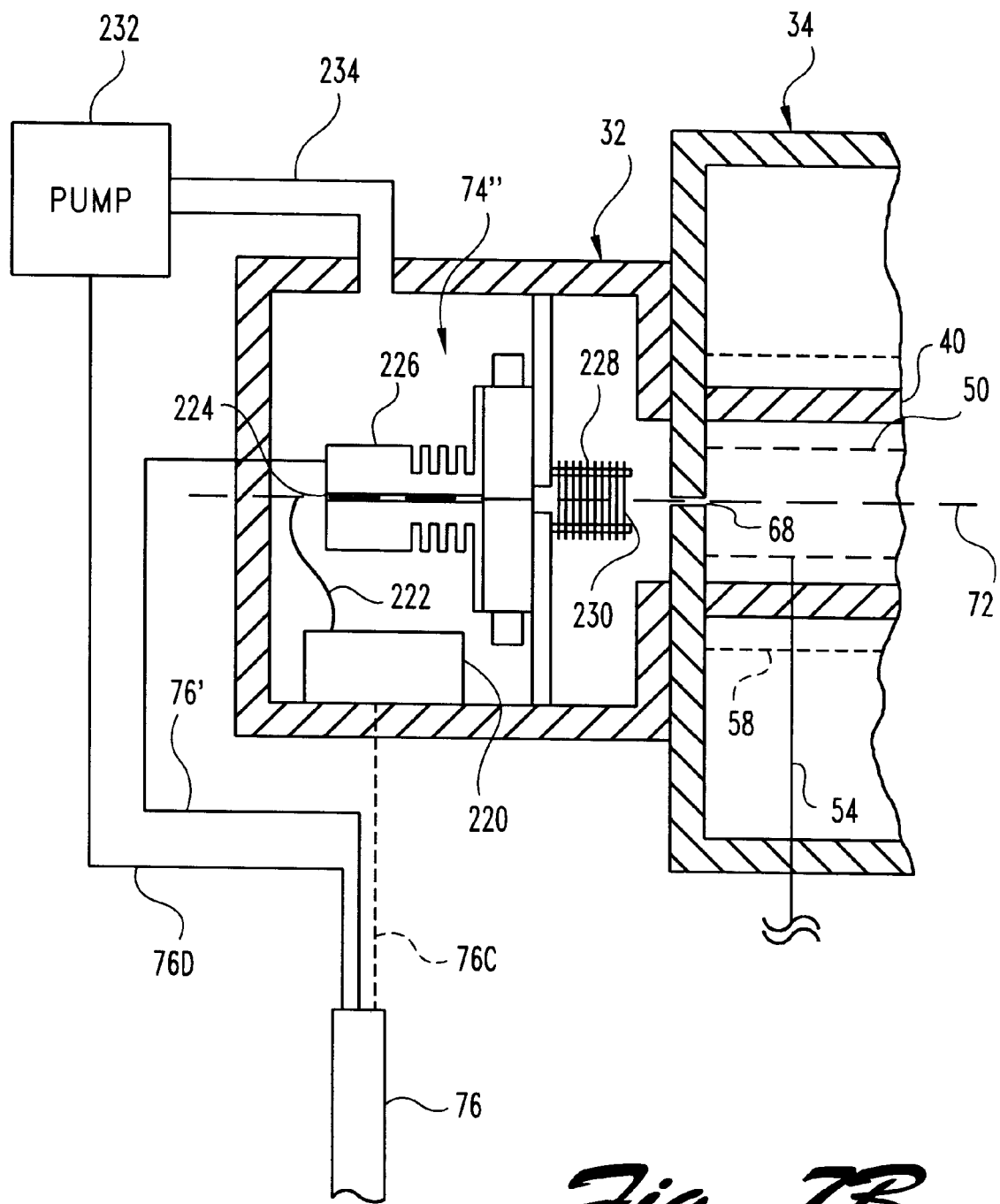
FIG. 7B is a diagrammatic illustration of an alternate embodiment of an ion source for use with either of the hybrid instruments shown in FIGS. 4 and 5.

Referring now to FIG. 7B, an alternate embodiment 74″ of an ion source 74 for either of the instrument embodiments of FIGS. 4 and 5, is shown. Embodiment 74″ includes a liquefied sample 220 having a spray hose or nozzle 222 extending toward an opening defined in a desolvation region 226. Actuation of the spray nozzle 222 may be manually controlled, as is known in the art, or may be controlled by computer 38 via signal path 76C. Desolvation region 226 is connected to computer 38 via signal path 76C', and is operable to convert charged sample droplets supplied thereto via nozzle 222 into gaseous ions and supply these ions to a ion optics member 228. Optics member 230 is operable to focus the gaseous ions and direct them into ion inlet opening of IMS 34. Ton source region 32 includes a conduit extending therefrom to a pump 232 which may be controlled by computer 38 via signal path 76D.

Ion source 74″ is a known electrospray ionization (ESI) arrangement operable to convert a liquefied solution containing the sample to gaseous ions. Computer 38 is operable to control activation times of desolvation region 226 to thereby control sample ionization events. Pump 232 is operable to pressurize the ion source region 32 as is known in the art, and the desolvation region 226 is operable convert the liquefied solution to gaseous ions. The sample source 220 may, in accordance with the present invention, include a solution containing a biomolecule of any size such as DNA, RNA, any of various proteins, carbohydrates, glycoconjugates, and the like.

Referring now to FIG. 7C, another alternate embodiment 74′″ CL an ion source 74 for either of the instrument embodiments of FIGS. 4 and 5, is shown. Embodiment 74′″ includes a sample source 236, which may be either of the foregoing sample sources 74' or 74″ illustrated in FIGS. 7A or 7B, and which may be controlled as described hereinabove by computer 38 via a number, M, of signal paths 76E, wherein M may be any integer less than N (see FIGS. 4 and 5).

Ic. source 74′″ further includes an ion trap 152 positioned between ion source 236 and the ion inlet opening 68 of IMS 34. Ion trap 152 is preferably a known quadrupole ion trap identical to that shown in FIG. 5 and described hereinabove. A detailed discussion of the operation of ion trap 152 therefore need not be repeated here. End cap 154 is connected to a voltage source VS9 238 via signal path 240, center ring is connected to a voltage source VS10 242 via signal path 244 and end cap 170 is connected to a voltage source VS11 246 vial signal path 248. VS9, VS10 and VS11 are each connected to computer 38 via signal paths 76F, 76G and 76H, respectively. Computer 38 is operable to control VS9, VS10 and VS11 identically as described with respect to VS6, VS7 and VS8, respectively, of FIG. 5.

In operation, computer 38 is operable to control ion trap 152, in a manner similar to that described hereinabove, to collect a bulk of ions therein and selectively eject the collected ions therefrom toward ion inlet opening 68 of IMS 34. As is known in the art, the peak resolution of an ion mobility instrument, such IMS 34, is limited by the length of the input pulse of ions into the instrument. Generally, mobility peaks cannot be resolved any better than the time length of the input ion pulse. A drawback particularly associated with the use of ESI is that the input ion pulse width must typically be at least 50 $\mu$s in order to produce enough ions for analysis. However, with the ion source arrangement 74′″ shown in FIG. 7C, computer 38 is operable to collect a large number of ions within ion trap 152 prior to pulsing the ions into the IMS 34. With a sufficient number of ions collected in ion trap 34, the only limitation on the ion input pulse length, and hence the resolution capability of IMS 34, is the time required to open and close ion trap 152. With existing ion traps, the ion. Input pulse lengths may be reduced to less than one us in duration.

Figure 8B:
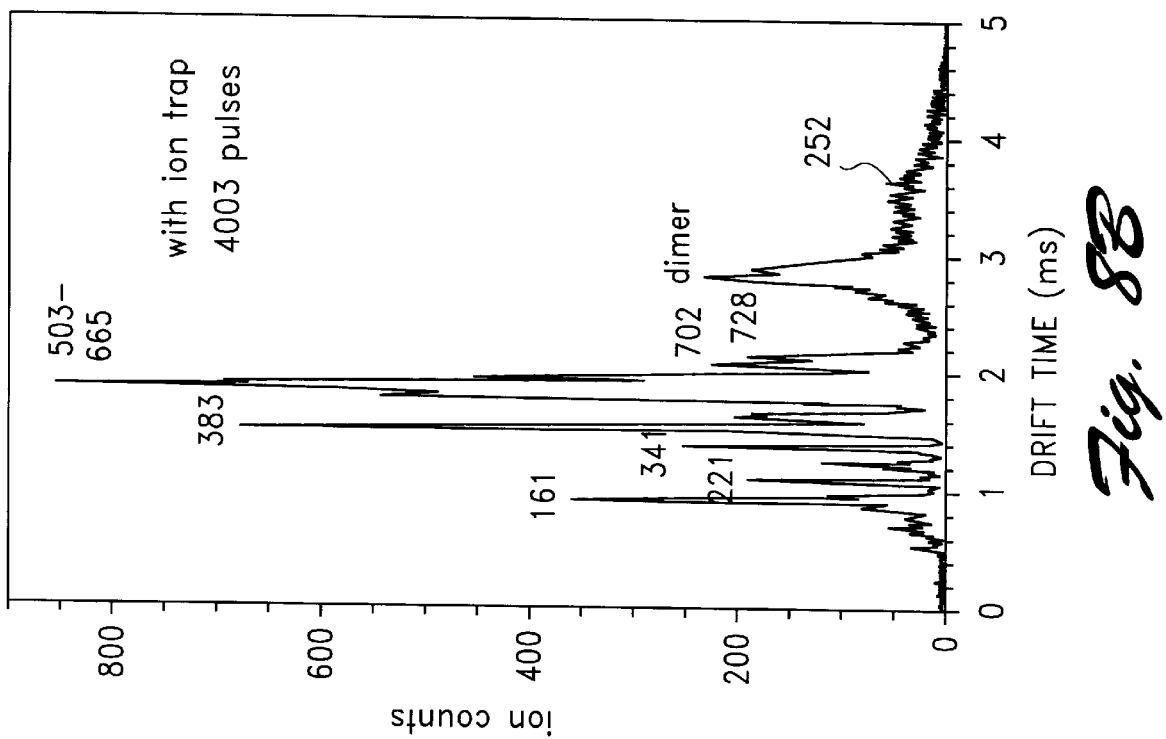
FIG. 8B is a plot of ion intensity vs ion drift time for an IMS instrument having an ion trap disposed between the ion source and the IMS instrument.
Figure 8A:
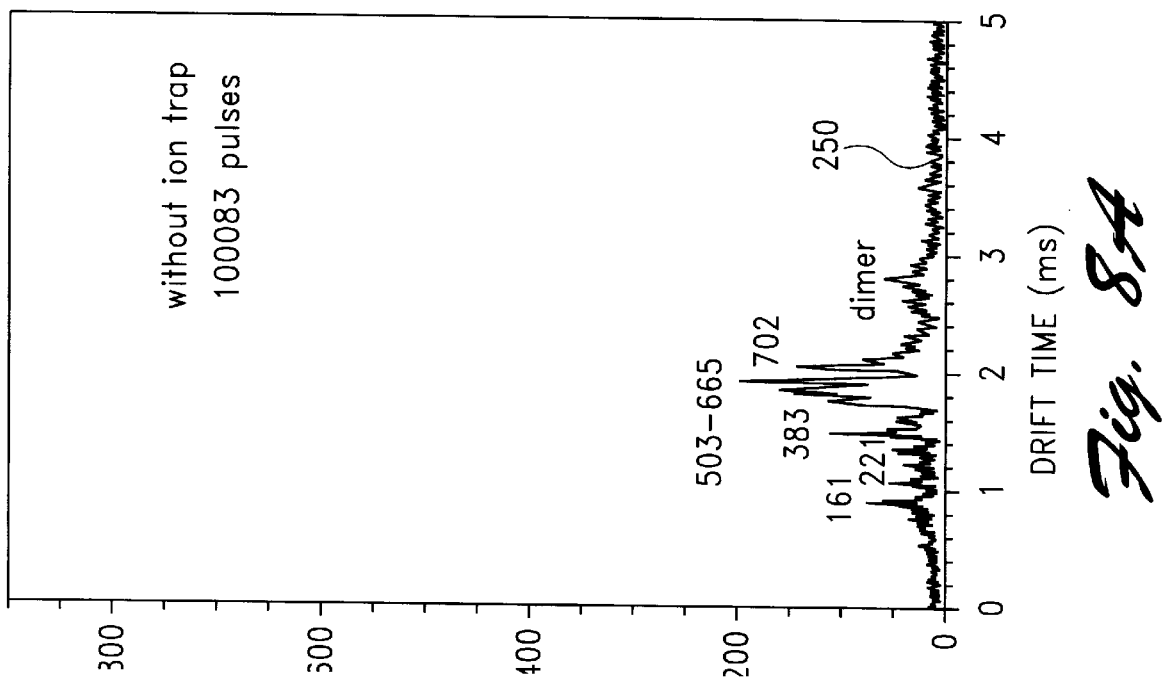
FIG. 8A is a plot of ion intensity vs ion drift time for an IMS instrument without an ion trap disposed between the ion source and the IMS instrument.

FIGS. 8A and 8B show a comparison of ion mobility distributions for a maltotetraose sample, wherein the spectrum 250 of FIG. 8A was produced using an ESI source similar to that shown in FIG. 7B, with 100,083 input pulses of 20 $\mu$s duration. The spectrum 252 of FIG. 8B was produced using the same ESI source as that used for FIG. 8A along with an ion trap, such as ion trap 152 shown in FIG. 7C, with 4003 pulses of 1 $\mu$s duration. Compared to spectrum 250, spectrum 252 has a 4–5 times increase in signal strength, an increase in resolution by a factor of approximately 20 and an increase in signal-to-noise ratio by a factor or approximately 20 as well.

Referring again to FIG. 7C, ion trap 152 may be used with any known ion generation source to increase not only the resolution and sensitivity of TMS 34 alone, but also the resolution and sensitivity of: either hybrid instrument 30 or 150 of FIGS. 4 and 5.

It is to be understood that either embodiment of the hybrid ion mobility and time-of-flight mass spectrometer shown and described herein is capable of operation in a number of different operational modes. For example, the structure and operation of the various embodiments of the present invention have been described herein according to a first mode of operation wherein ions of relatively low energy are generated and injected into the hybrid instrument, from which structural information relating to the ions can be obtained.

In a second mode of operation, such ions could be injected into the hybrid instrument at higher energies, wherein high energy collisions with the buffer gas within the IMS 34 result in ion fragmentation. In such a case, the ion fragments, separated in time as a function of their mobilities, would be supplied to the TOFMS portion of the instrument, wherein mass spectra information of the various fragments could be obtained for sequencing analysis. Alternatively, fragmentation of ions for such analysis may be accomplished via any of a number of other known techniques. Examples of such known alternative ion fragmentation techniques include enzyme degradation fragmentation, photo-fragmentation, thermal dissociation such as by heating drift tube 40 via control of variable temperature source 60, electron impact dissociation, surface induced dissociation, and blackbody infrared radiation induced dissociation.

In a third mode of operation, ions of only a particular mass could be processed by the hybrid instrument. One way of generating ions of only a particular mass is to adjust the peak amplitude and/or dc voltage of the center ring voltage source of an ion trap positioned prior to the IMS 34. By properly adjusting this voltage, ion trap 152 may be configured to store therein only ions having a particular mass to charge ration. In this manner, the ion trap 152 is controlled to act as an ion filter. Another way of analyzing ions of only a particular mass is to provide an ion trap 152 between the IMS 34 and TOFMS 36, and controlling the ion trap 152 as just discussed to filter out ions having undesirable mass to charge ratios.

In a fourth mode of operation, high energy ions of only a particular mass are introduced into the IMS 34. Therein, these ions undergo fragmentation, and such fragments could then be further processed by the TOFMS 36 as discussed above.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method of generating ion mass spectral information, comprising the steps of:

generating a gaseous bulk of ions;

separating the gaseous bulk of ions in time along a first axis to form a number of ion packets each having a unique ion mobility associated therewith;

sequentially separating at least some of the ion packets in time along a second axis perpendicular to the first axis to form a number of ion subpackets each having a unique ion mass associated therewith; and processing at least some of the ion subpackets to determine mass spectral information therefrom.

2. The method of claim 1 wherein the step of generating a gaseous bulk of ions includes generating the gaseous bulk of ions from a liquefied biological sample.

3. The method of claim 2 wherein the step of generating a gaseous bulk of ions from a liquefied biological sample includes generating the gaseous bulk of ions via electrospray ionization.

4. The method of claim 1 wherein the step of generating ions includes desorbing the gaseous bulk of ions from a surface of a biological sample.

5. The method of claim 4 wherein the step of desorbing the gaseous bulk of ions from a surface of a biological sample includes generating the gaseous bulk of ions via laser desorption ionization.

6. The method of claim 1 wherein the step of generating a gaseous bulk of ions includes the steps of:

generating gaseous ions from a sample source;

collecting at least some of the generated ions in an ion trap;

repeating the generating and collecting steps a number of times to thereby form a gaseous bulk of ions in the ion trap; and releasing the gaseous bulk of ions from the ion trap.

7. The method of claim 6 wherein the step of generating gaseous ions from a sample source includes generating the gaseous ions from a biological sample.

8. The method of claim 7 wherein the step of generating gaseous ions from a biological sample includes generating the gaseous ions from the biological sample via electrospray ionization.

9. The method of claim 7 wherein the step of generating gaseous ions from a biological sample includes generating the gaseous ions from the biological sample via laser desorption ionization.

10. Apparatus for generating mass spectral information from a sample source, comprising:

means for generating a gaseous bulk of ions from a sample source;

an ion mobility spectrometer (IMS) defining an ion inlet opening at one end thereof in fluid communication with said means for generating a gaseous bulk of ions and an ion outlet opening at an opposite end thereof, said ion inlet and outlet openings defining a first axis therebetween; and a time-of-flight mass spectrometer (TOFMS) defining an ion acceleration region at one end thereof in fluid communication with said ion outlet opening and an ion detector at an opposite end thereof, said ion acceleration region and said ion detector defining a second axis therebetween perpendicular to said first axis.

11. The apparatus of claim 10 further including means for controlling said means for generating a gaseous bulk of ions and said ion acceleration region.

12. The apparatus of claim 11 wherein said means generating a bulk of ions is responsive to a first signal supplied by said means for controlling to generate said bulk of ions, and said acceleration region is responsive to a second signal supplied by said means for controlling to activate said acceleration region.

13. The apparatus of claim 12 wherein said ion detector is operable to produce detector output signals indicative of detection of ions thereat;

and wherein said means for controlling is responsive to said detector output signals to compute ion mass spectral information corresponding thereto.

14. The apparatus of claim 10 wherein said IMS further includes a drift tube situated between said ion inlet and outlet openings, said first axis extending through said drift tube and defining a drift tube axis;

and wherein said TOFMS further includes a flight tube situated between said ion acceleration region and said ion detector, said second axis extending through said flight tube and defining a flight tube axis.

15. The apparatus of claim 14 wherein said IMS further includes means for providing said drift tube with a pressurized buffer gas therein.

16. The apparatus of claim 10 further including:

a first pump associated with said IMS, said first pump operable to maintain a first predefined pressure within said IMS; and a second pump associated with said TOFMS, said second pump operable to maintain a second predefined pressure within said TOFMS.

17. The apparatus of claim 10 wherein said sample source is a biological sample.

18. A method of generating ion mass spectral information, comprising the steps of:

generating a gaseous bulk of ions;

separating the gaseous bulk of ions in time along a first axis to form a number of ion packets each having a unique ion mobility associated therewith;

sequentially collecting said ion packets in, and ejecting ion packets from, a first ion trap;

sequentially separating in time at least some of the ion packets ejected from the first ion trap along a second axis to form a number of ion subpackets each having a unique ion mass associated therewith; and processing at least some of the ion subpackets to determine mass spectral information therefrom.

19. The method of claim 18 wherein the step of generating a gaseous bulk of ions includes generating the gaseous bulk of ions from a liquefied biological sample.

20. The method of claim 19 wherein the step of generating a gaseous bulk of ions from a liquefied biological sample includes generating the gaseous bulk of ions via electrospray ionization.

21. A The method of claim 18 wherein the step of generating ions includes desorbing the gaseous bulk of ions from a surface of a biological sample.

22. The method of claim 21 wherein the step of desorbing the gaseous bulk of ions from a surface of a biological sample includes generating the gaseous bulk of ions via laser desorption ionization.

23. The method of claim 18 wherein the step of generating a gaseous bulk of ions includes the steps of:
generating gaseous ions from a sample source;
collecting at least some of the generated ions in a second ion trap;
repeating the generating and collecting steps a number of times to thereby form a gaseous bulk of ions in the second ion trap; and
releasing the gaseous bulk of ions from the second ion trap.

24. The method of claim 23 wherein the step of generating gaseous ions from a sample source includes generating the gaseous ions from a biological sample.

25. The method of claim 24 wherein the step of generating gaseous ions from a biological sample includes generating the gaseous ions from the biological sample via electrospray ionization.

26. The method of claim 24 wherein the step of generating gaseous ions from a biological sample includes generating the gaseous ions from the biological sample via laser desorption ionization.

27. Apparatus for generating mass spectral information from a sample source, comprising:
means for generating a gaseous bulk of ions from a sample source;
an ion mobility spectrometer (IMS) defining an ion inlet opening at one end thereof in fluid communication with said means for generating a gaseous bulk of ions and an ion outlet opening at an opposite end thereof, said ion inlet and outlet openings defining a first axis therebetween;
an ion trap defining an ion inlet in fluid communication with the ion outlet opening of said IMS and an ion outlet; and
a mass spectrometer (MS) defining an ion acceleration region at one end thereof in fluid communication with said ion outlet of said ion trap and an ion detector at an opposite end thereof, said ion acceleration region and said ion detector defining a second axis therebetween.

28. The apparatus of claim 27 further including means for controlling said means for generating a gaseous bulk of ions, said ion trap and said ion acceleration region.

29. The apparatus of claim 28 wherein said means generating a bulk of ions is responsive to a number of ion source signals supplied by said means for controlling to generate said bulk of ions.

30. The apparatus of claim 29 wherein said ion trap is responsive to a number of ion trap signals supplied by said means for controlling to allow entrance of ions therein, maintain ions therein and eject ions therefrom.

31. The apparatus of claim 30 wherein said acceleration region is responsive to a number of ion acceleration signals supplied by said means for controlling to control activation of said acceleration region.

32. The apparatus of claim 31 wherein said ion detector is operable to produce detector output signals indicative of detection of ions thereat;
and wherein said means for controlling is responsive to said detector output signals to compute ion mass spectral information corresponding thereto.

33. The apparatus of claim 27 wherein said IMS further includes a drift tube situated between said ion inlet and outlet openings, said first axis extending through said drift tube and defining a drift tube axis;
and wherein said MS is a time-of-flight mass spectrometer (TOFMS) including a flight tube situated between said ion acceleration region and said ion detector, said second axis extending through said flight tube and defining a flight tube axis.

34. The apparatus of claim 33 wherein said drift tube axis and said flight tube axis are non-perpendicular.

35. The apparatus of claim 33 wherein said IMS further includes means for providing said drift tube with a pressurized buffer gas therein.

36. The apparatus of claim 28 further including:
a first pump associated with said IMS, said first pump operable to maintain a first predefined pressure within said IMS; and
a second pump associated with said MS, said second pump operable to maintain a second predefined pressure within said TOFMS.

37. The apparatus of claim 27 wherein said sample source is a biological sample.

38. Apparatus for generating mass spectral information from a sample source, comprising:
means for generating a gaseous bulk of ions from a sample source;
a first ion trap defining an ion inlet in fluid communication with said means for generating a gaseous bulk of ions and an ion outlet;
an ion mobility spectrometer (IMS) defining an ion inlet opening at one end thereof in fluid communication with said ion outlet of said first ion trap and an ion outlet opening at an opposite end thereof, said ion inlet and outlet openings defining a first axis therebetween; and
a mass spectrometer (MS) defining an ion acceleration region at one end thereof in fluid communication with said ion outlet opening of said IMS and an ion detector at an opposite end thereof, said ion acceleration region and said ion detector defining a second axis therebetween.

39. The apparatus of claim 38 wherein said first axis is perpendicular to said second axis.

40. The apparatus of claim 38 wherein said first axis is non-perpendicular to said second axis;
and further including a second ion trap situated between said IMS and said MS, said second ion trap having an ion inlet in fluid communication with said ion outlet opening of said IMS and an ion outlet in fluid communication with said ion acceleration region of said MS.

41. The apparatus of claim 38 wherein said IMS further includes a drift tube situated between said ion inlet and outlet openings, said first axis extending through said drift tube and defining a drift tube axis;
and wherein said MS is a time-of-flight mass spectrometer (TOFMS) including a flight tube situated between said ion acceleration region and said ion detector, said second axis extending through said flight tube and defining a flight tube axis.

42. The apparatus of claim 40 wherein said IMS further includes means for providing said drift tube with a pressurized buffer gas therein.

43. The apparatus of claim 41 further including:
a first pump associated with said IMS, said first pump operable to maintain a first predefined pressure within said IMS; and a second pump associated with said TOFMS, said second pump operable to maintain a second predefined pressure within said TOFMS.

44. The apparatus of claim 38 wherein said sample source is a biological sample.

45. A method of generating ion mass spectral information, comprising the steps of:

generating gaseous ions from a sample source;

collecting at least some of the generated ions in an ion trap;

repeating the generating and collecting steps a number of times to thereby form a gaseous bulk of ions in the ion trap;

releasing the gaseous bulk of ions from the ion trap;

separating the gaseous bulk of ions in time along a first axis to form a number of ion packets each having a unique ion mobility associated therewith;

sequentially separating in time at least some of the ion packets along a second axis to form a number of ion subpackets each having a unique ion mass associated therewith; and processing at least some of the ion subpackets to determine mass spectral information therefrom.

46. The method of claim 45 wherein the step of generating ions from a sample source includes generating ions from a biological sample.

\* \* \* \* \*

UNITED STATES PATENT AND TRADEMARK OFFICE
CERTIFICATE OF CORRECTION

PATENT NO. : 5,905,258

DATED : May, 18, 1999

INVENTOR(S) : David E. Clemmer, James P. Reilly

It is certified that error appears in the above-identified patent and that said Letters Patent is hereby corrected as shown below:

Col. 1, line 8
 replace "mess-to-charge"
 with --mass-to-charge--
Col. 1, line 45
 replace "riot"
 with --not--
Col. 3, line 7
 replace "TMS"
 with --IMS--
Col. 4, line 17
 replace "out let"
 with --outlet--
Col. 7, line 49
 replace "TMS"
 with --IMS--
Col. 8, line 40
 replace "teat"
 with --that--

Col. 8, line 42
 replace "places"
 with --plates--
Col. 9, line 12
 replace "5,504,26"
 with --5,504,326--
Col. 11, line 53
 replace "152"
 with --162--
Col. 11, line 63
 replace "Tons"
 with --Ions--
Col. 12, line 33
 replace "draft"
 with --drift--
Col. 13, line 23
 replace "Ton"
 with --Ion--

Col. 13, line 47
 replace "Ic."
 with --Ion--
Col. 14, line 13
 replace "ion.Input"
 with --ion input--
Col. 14, line 26
 replace "or"
 with --of--

Signed and Sealed this

Twenty-first Day of December, 1999

Attest:

Q. TODD DICKINSON

*Attesting Officer*    *Acting Commissioner of Patents and Trademarks*